Figure 1:
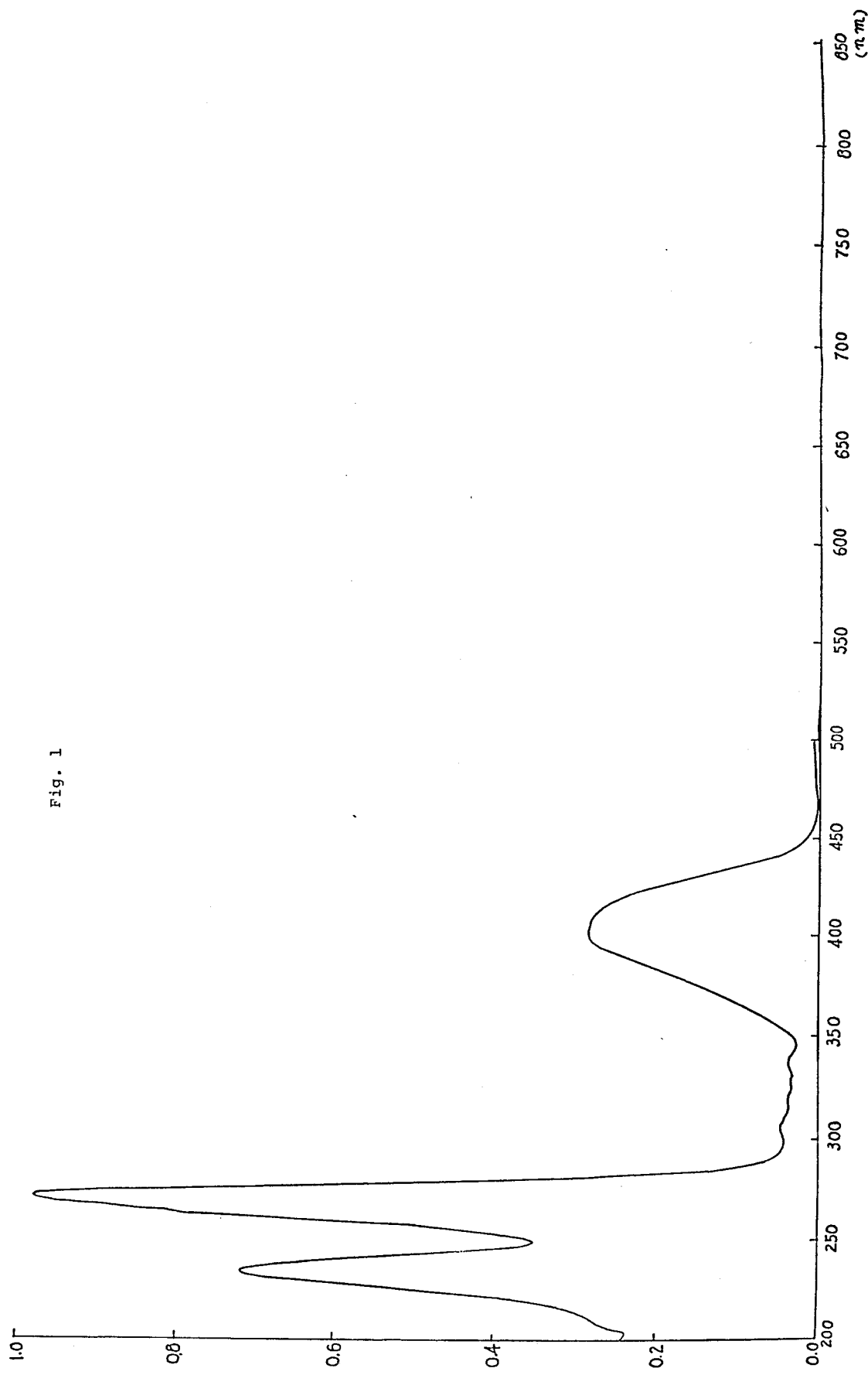

United States Patent [19]

Shirahata et al.

[11] Patent Number: 4,459,291

[45] Date of Patent: Jul. 10, 1984

[54] COMPOUNDS HAVING ANTIBIOTIC ACTIVITY, PROCESSES FOR THEIR PREPARATION, PHARMACEUTICAL COMPOSITIONS CONTAINING THEM AND THEIR USE AS MEDICAMENTS

[75] Inventors: Kunikatsu Shirahata, Machida; Takao Iida, Tokyo, both of Japan

[73] Assignee: Kyowa Hakko Kogyo Kabushiki Kaisha, Ohte, Japan

[21] Appl. No.: 400,537

[22] Filed: Jul. 21, 1982

[30] Foreign Application Priority Data

Jul. 22, 1981 [JP] Japan ................................ 56-113601

[51] Int. Cl.$^3$ ...................... C07H 15/24; A61K 31/71; A61K 31/35; C07D 311/02
[52] U.S. Cl. ................................. 424/180; 536/18.1; 549/332; 424/283
[58] Field of Search ....................... 424/180; 536/18.1; 549/332

[56] References Cited

U.S. PATENT DOCUMENTS 4,259,476  3/1981  Kende et al. ..................... 536/18.1

FOREIGN PATENT DOCUMENTS 29309  5/1981  European Pat. Off. .

OTHER PUBLICATIONS

Ando et al., Synthesis of Mycophenolic Acid B-D Glucuronide and its Antitumor Activity, J. of Antibiotics, vol. XXIII, No. 8.

Raghunathan et al., "Chrysophonol-I-$\beta$-Gentiobioside, a New Anthroquinone Glycoside from *Cassia tora* Linn", Indian Journal of Chemistry, vol. 12, pp. 1251–1253.

*Primary Examiner*—Donald B. Moyer
*Assistant Examiner*—C. Joseph Faraci
*Attorney, Agent, or Firm*—Wolder, Gross & Yavner

[57] ABSTRACT

New antibacterial compounds, DC—45—$A_1$ and DC—45—$A_2$ are produced by fermentation of a microorganism belonging to the genus Streptomyces. The antibiotics are accumulated in the culture liquor and are isolated therefrom. These compounds are also prepared by acid hydrolysis of known compounds, DC—45—A or DC—45—$B_2$. DC—45—$A_2$ is also prepared by acid hydrolysis of DC—45—$A_1$.

5 Claims, 4 Drawing Figures

COMPOUNDS HAVING ANTIBIOTIC ACTIVITY, PROCESSES FOR THEIR PREPARATION, PHARMACEUTICAL COMPOSITIONS CONTAINING THEM AND THEIR USE AS MEDICAMENTS

The present invention relates to compounds having antibiotic activity, processes for their preparation, pharmaceutical compositions containing them and their use as medicaments.

In Japanese Patent Application No. 137,734/79 [as laid open to public inspection as Kokai Koho Sho-56-61398 (61398/81) on May 26, 1981] and in European Patent Application No. 80303807.4 we describe certain substances having antibiotic activity (which substances we designate DC-45-A, DC-45-B, and DC-45-$B_2$) which may be obtained by culturing a microorganism of the genus Streptomyces, preferably *Streptomyces bottropensis* (formerly designated *Streptomyces ochraceus*) (FERM-P No. 5219; NRRL 12051). The physicochemical and antibiotic characteristics of DC-45-A, DC-45-$B_1$ and DC-45-$B_2$ are described in the aforementioned Japanese and European Patent Applications.

The substances DC-45-A, DC-45-$B_1$ and DC-45-$B_2$ are represented by the following general formula (A):

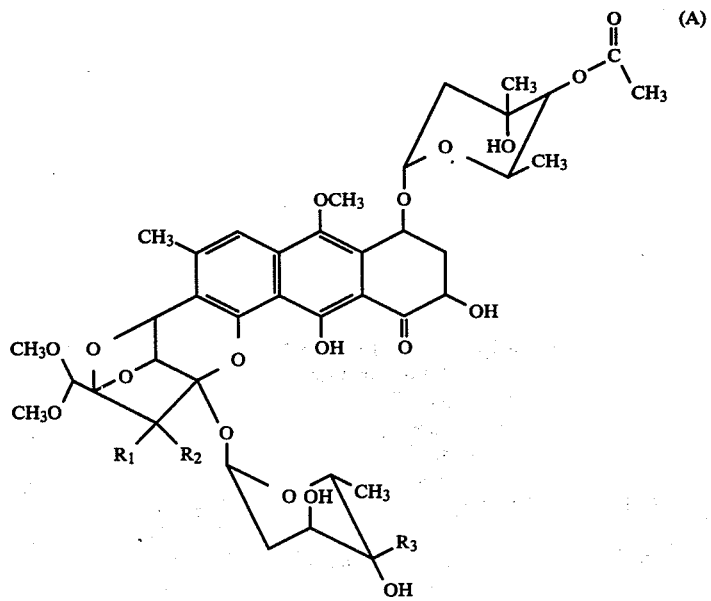

wherein (i) $R_1$ and $R_2$ together with the carbon atom therebetween represent the group

and $R_3$ represents

(designated DC-45-A); (ii) $R_1$ represents —OH, $R_2$ represents —$CH_2OH$ and $R_3$ represents

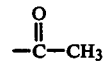

(designated DC-45-$B_1$); or (iii) $R_1$ and $R_2$ together with the carbon atom therebetween represent the group

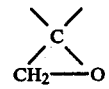

and $R_3$ represents

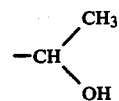

(designated DC-45-$B_2$).

The present invention is based upon the discovery that new substances which we have now recovered from the cultured broth obtained by culturing the said strain of *Streptomyces bottropensis* (FERM-P No. 5219; NRRL 12051) possess interesting physiological activity and in particular antibiotic activity.

According to one feature of the present invention, therefore, we provide a compound having antibiotic activity and possessing the formula (I):

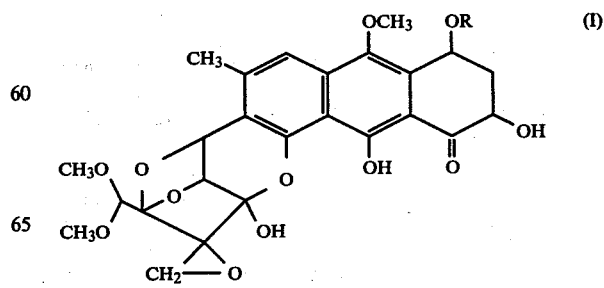

[wherein R represents the group:

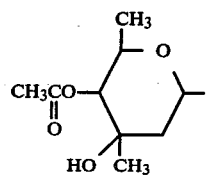

or a hydrogen atom] or a salt thereof.

The substances of the general formula (I) have been designated by us as DC-45-A$_1$ and DC-45-A$_2$. The physico-chemical characteristics of DC-45-A$_1$ and DC-45-A$_2$ are as follows:

The physico-chemical characteristics of DC-45-A$_1$ represented by the following formula (II):

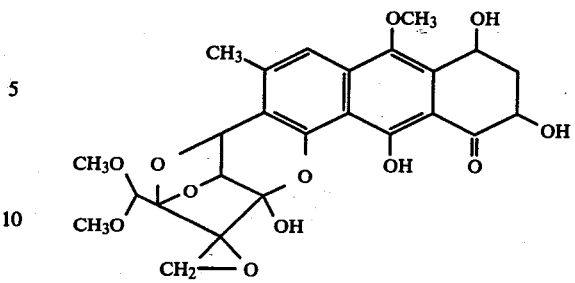

are as follows:
(1) Melting point: 152°–158° C. (Decomp.)
(2) Elemental analysis (%): H 5.23, C 57.80
(3) Molecular weight: 518

Figure 2:
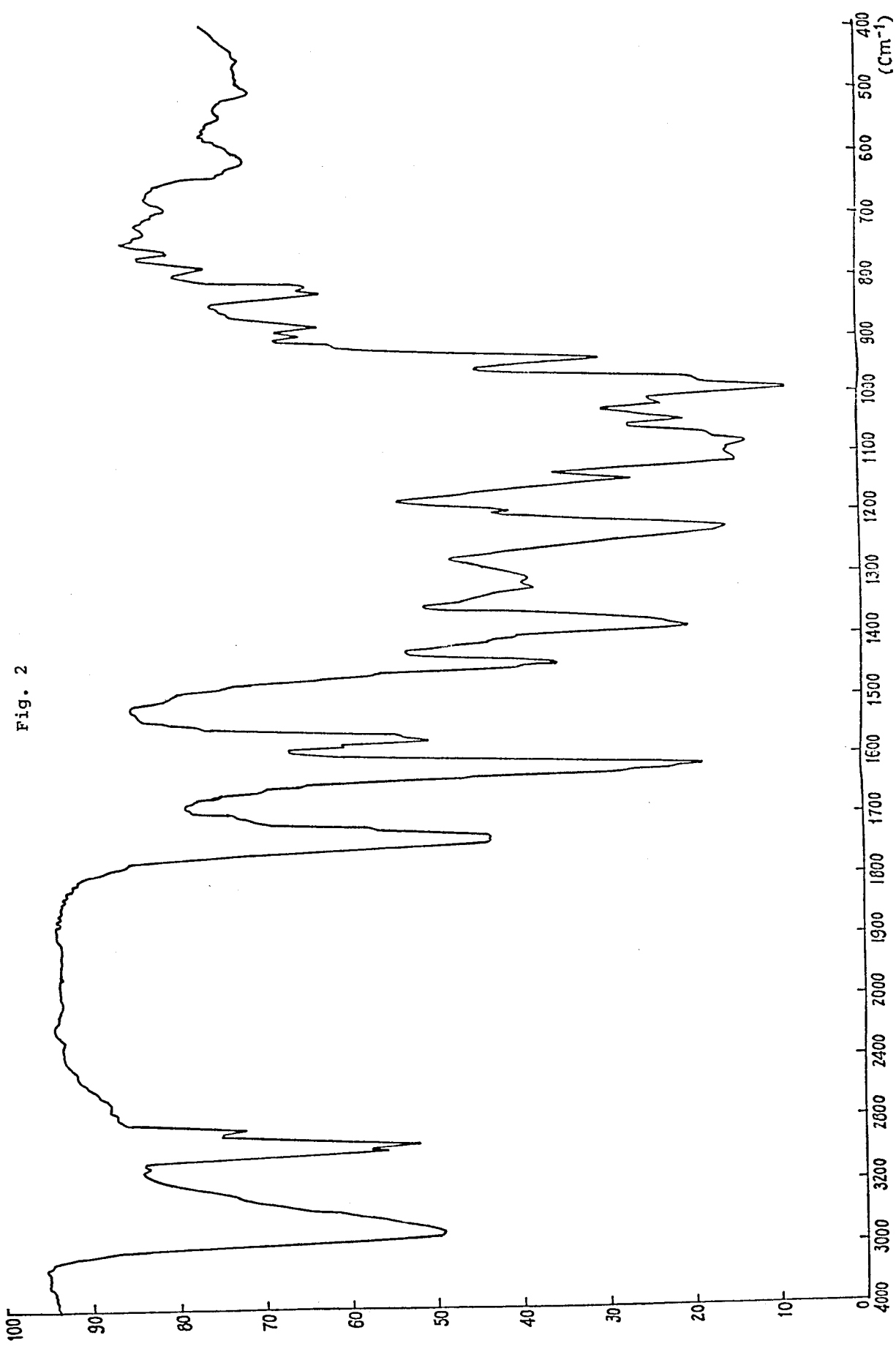

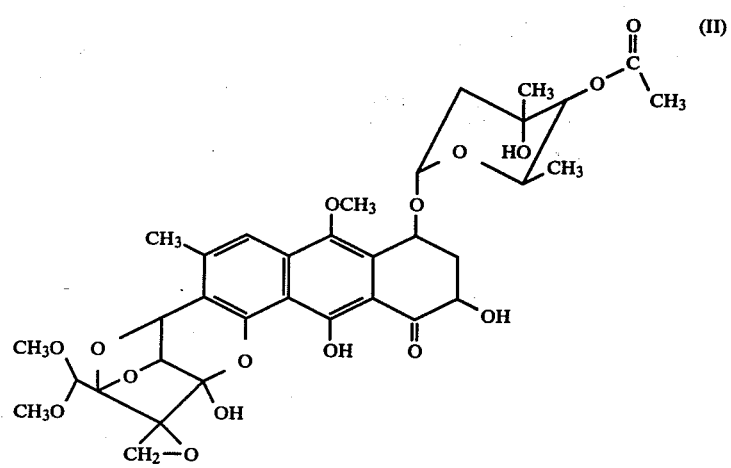

are as follows:
(1) Melting point: 184°–186° C. (Decomp.)
(2) Elemental analysis (%): H 5.96, C 57.77
(3) Molecular weight: 704
(4) Molecular formula: $C_{34}H_{40}O_{16}$
(5) Ultraviolet absorption spectrum. As shown in FIG. 1 (in methanol)
(6) Infrared absorption spectrum: As shown in FIG. 2 (by KBr method)
(7) Specific rotation: $[\alpha]_D^{25} = +103°$ (c=0.5, CHCl$_3$)
(8) PMR spectrum (in CDCl$_3$, TMS standard) (ppm): 1.07 (3H,s); 1.24 (3H, dJ=6.4); many peaks between 1.50–2.50; 2.14 (3H,s); 2.60 (3H, s): 3.02 (1H, dJ=5.4); 3.13 (1H, DJ=5.4); 3.46 (3H,s); 3.63 (3H,s); 3.84 (3H,s); many peaks between 4.50–5.50; 7.43 (1H,s); 14.3 (1H,s)

CMR spectrum (in CDCl$_3$, TMS standard) (ppm): 16.9; 20.5; 20.9; 25.7; 36.7 (dual); 50.2; 56.6; 57.0; 62.7; 63.0; 68.0; (dual); 68.9; 69.2; 69.4; 73.3; 74.4; 98.3; 99.0; 100.1; 104.1; 107.4; 114.8; 115.4; 116.7; 126.5; 135.4; 143.0; 144.9; 151.6; 163.0; 170.4; 203.1

(10) Solubility: Soluble in methanol, ethanol, acetone, ethyl acetate and chloroform, soluble with difficulty in benzene and aqueous ether, and insoluble in n-hexane.

Figure 3:
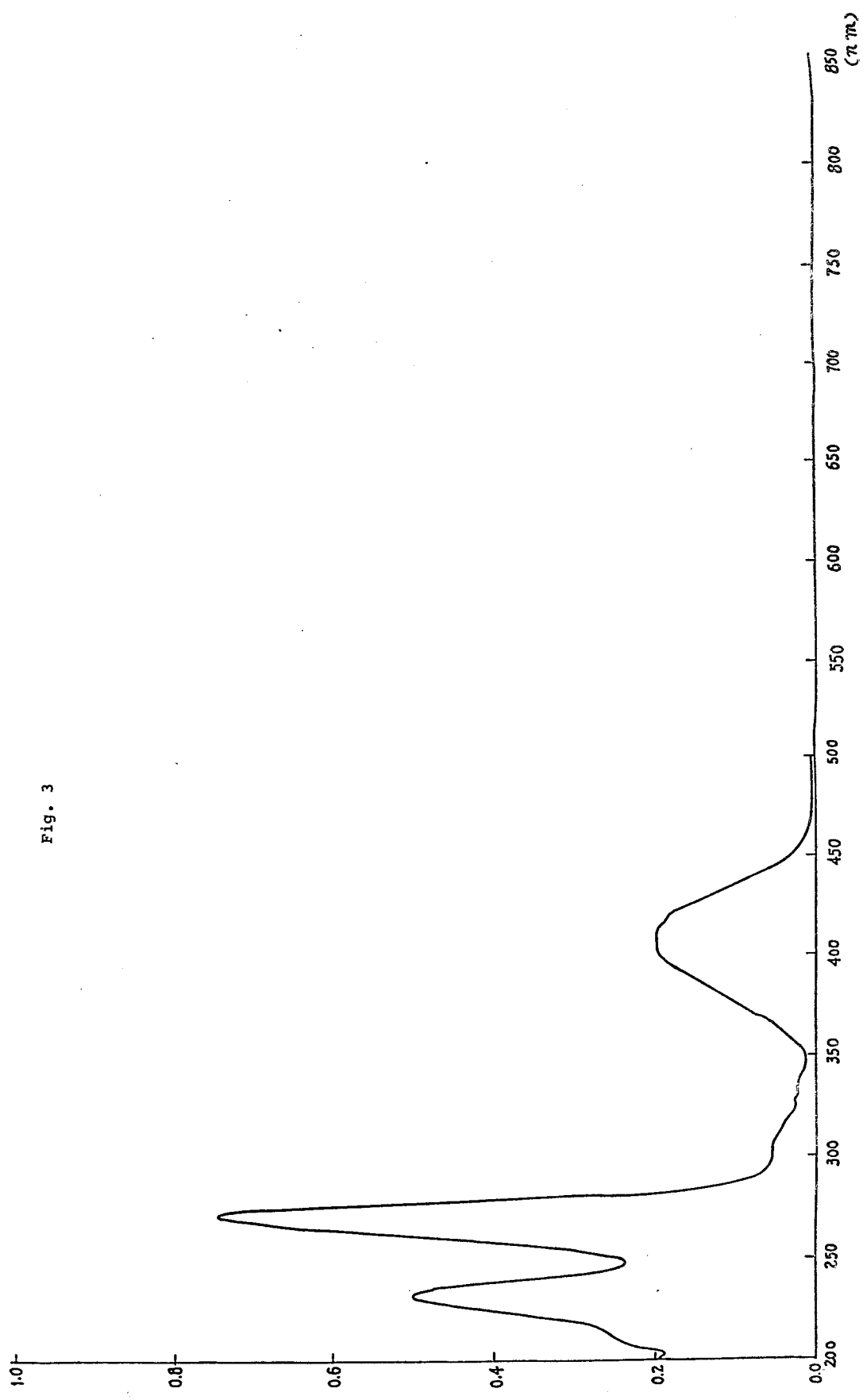
Figure 4:
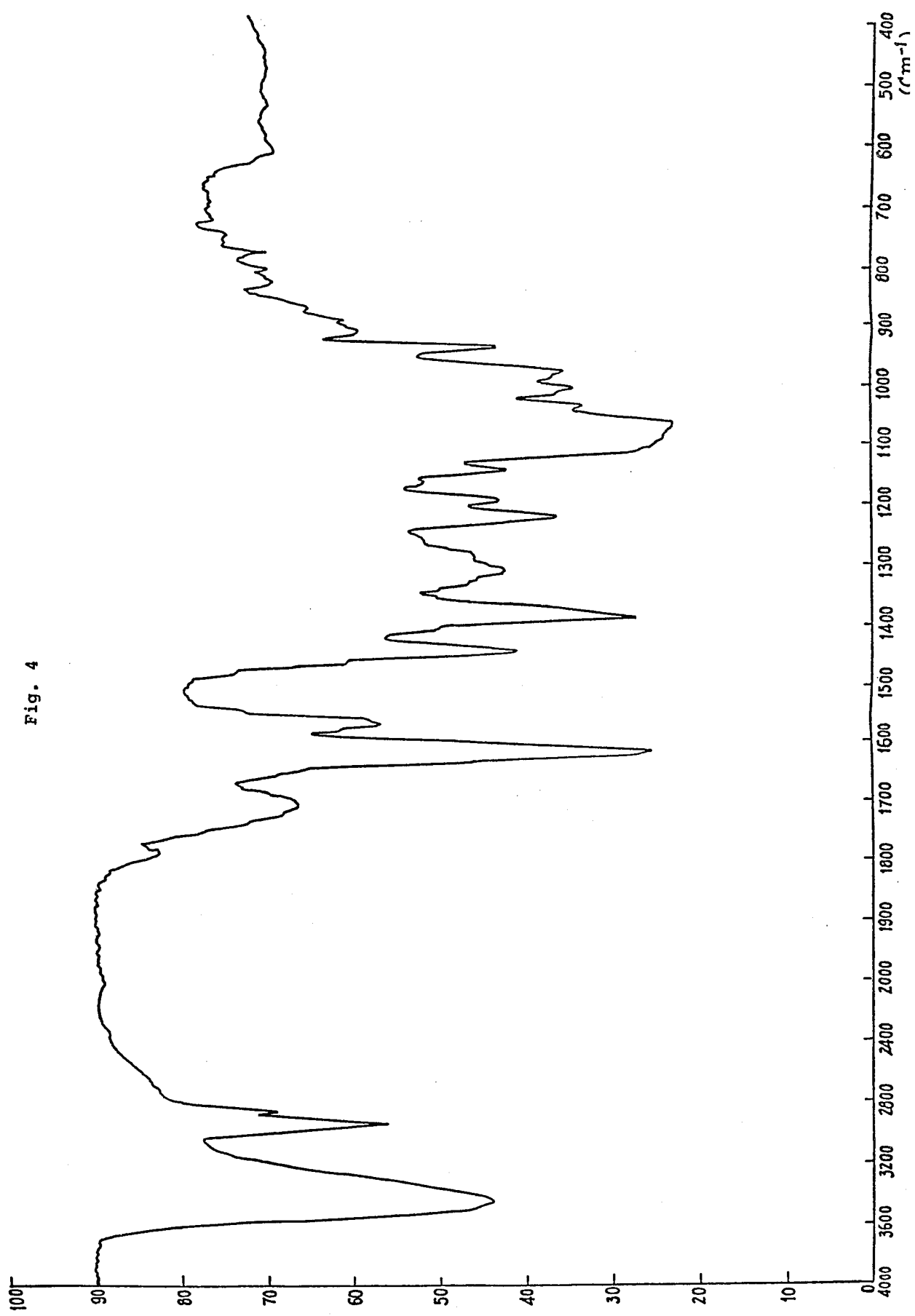

The physico-chemical characteristics of DC-45-A$_2$ represented by the following formula:

(4) Molecular formula: $C_{25}H_{26}O_{12}$
(5) Ultraviolet absorption spectrum: As shown in FIG. 3 (in methanol)
(6) Infrared absorption spectrum: As shown in FIG. 4 (by KBr method)
(7) Specific rotation: $[\alpha]_D^{25} = +97.5°$ (c=0.5, CHCl$_3$)
(8) PMR spectrum (in CDCl$_3$, TMS standard) (ppm): Many peaks between 1.50–2.50; 2.61 (3H,s); 3.01 (1H, dJ=4.6); 3.13 (1H, dJ=4.6); 3.46 (3H, s); 3.62 (3H,s); 3.92 (3H,s); many peaks between 4.50–5.50; 7.43 (1H,s); 14.0 (1H,s)
(9) CMR spectrum (in CDCl$_3$, TMS standard): 20.5; 37.3; 50.0; 56.6; 57.0; 61.8; 63.1; 67.8; 69.1; 69.4; 73.4; 99.0; 100.0; 104.0; 107.4; 114.3; 115.1; 116.2; 129.3; 135.5; 142.6; 144.3; 151.4; 162.1; 203.6
(10) Solubility: Soluble in methanol, ethanol, acetone, ethyl acetate and chloroform, soluble with difficulty in benzene, ether and water, and insoluble in n-hexane.

The compounds of formula I (DC-45-A$_1$ and DC-45-A$_2$) and the salts thereof may for example be in substantially pure form.

The Rf values of DC-45-A$_1$ and DC-45-A$_2$ are shown in Table 1, in which the Rf values were determined by thin layer chromatography using silica gel (Kieselgel 60 Art 5721, commercial product of E. Merck, West Germany) and developed for 3 hours at room temperature.

TABLE 1

| No. | Substance | Rf value |
|---|---|---|
| I. Chloroform/methanol = 90:1 v/v | DC-45-A | 0.85 |
| | DC-45-$B_1$ | 0.50 |
| | DC-45-$B_2$ | 0.45 |
| | DC-45-$A_1$ | 0.71 |
| | DC-45-$A_2$ | 0.44 |
| II. Ethyl acetate/acetic acid = 90:1 v/v | DC-45-A | 0.70 |
| | DC-45-$B_1$ | 0.25 |
| | DC-45-$B_2$ | 0.35 |
| | DC-45-$A_1$ | 0.71 |
| | DC-45-$A_2$ | 0.46 |

FIGS. 1 and 2 show respectively the ultraviolet and infrared absorption spectra of DC-45-$A_1$. FIGS. 3 and 4 show respectively the ultraviolet and infrared absorption spectra of DC-45-$A_2$.

DC-45-$A_1$ and DC-45-$A_2$ can each form salts with metals such as alkali metals, alkaline earth metals and aluminium. For pharmaceutical use the salts of DC-45-$A_1$ and DC-45-$A_2$ will be pharmacologically acceptable such as the sodium, potassium, calcium, magnesium and aluminium salts. Other salts may however be used for example in the preparation of the pharmacologically acceptable salts. Such a salt may for example be prepared by reacting DC-45-$A_1$ or DC-45-$A_2$ with an appropriate metal hydroxide or alkoxide.

$LD_{50}$ of DC-45-$A_1$ is 0.375 (mg/kg) for i.p. and i.v. and that of DC-45-$A_2$ is 5.8 (mg/kg) for i.p. and 14.0 (mg/kg) for i.v.

As stated above the compounds DC-45-$A_1$ and DC-45-$A_2$ possess antibiotic activity and this activity is shown in Table 2, the activity being determined by the agar dilution method at pH 7.0.

TABLE 2

| | Minimun Inhibitory Concentration (µg/ml) | |
|---|---|---|
| | DC-45- | |
| Microorganism tested | $A_1$ | $A_2$ |
| Staphylococcus aureus ATCC 6538P | 0.4 | 100 |
| Bacillus subtilis No. 10707 | 0.04 | 100 |
| Klebsiella pneumoniae ATCC 10031 | 0.4 | 12 |
| Salmonella typhosa ATCC 9992 | 50 | 50 |
| Escherichia coli ATCC 26 | 12 | 25 |

According to a further feature of the present invention, there is provided a process for preparing a compound of the invention hereinbefore defined (and designated DC-45-$A_1$ and DC-45-$A_2$), which process comprises culturing a microorganism of the genus Streptomyces and capable of producing a compound of the invention as hereinbefore defined in a culture medium to accumulate a compound of the invention as hereinbefore defined in the culture broth and recovering the said compound of the invention therefrom.

Although any and all microorganisms of the genus Streptomyces capable of producing DC-45-$A_1$ and/or DC-45-$A_2$ may be used for the purpose of the present invention, it is preferred to use microorganisms of the species Streptomyces bottropensis (formerly designated Streptomyces ochraceus (DC-45) (FERM-P No. 5219; NRRL 12051) or a mutant thereof capable of producing DC-45-$A_1$ and/or DC-45$A_2$. The taxonomic characteristics of FERM-P NO. 5219 are disclosed in European Patent Application No. 80303807.4 and Japanese Patent Application 137,734/79 referred to hereinbefore.

Streptomyces bottropensis (FERM-P No. 5219; NRRL 12051) was filled with the NRRL on Oct. 6, 1979 and became available to the public on Oct. 9, 1979. As stated above any mutant strain of Streptomyces bottropensis (FERM-P No. 5219; NRRL 12051) capable of producing DC-45-$A_1$ and/or DC-45-$A_2$ may be used in the process of the present invention, such mutants being obtained for example by conventional mutation processes e.g. mutagenic chemicals or mutagenic radiation.

Various methods used conventionally for culturing the microorganisms of the genus Streptomyces may, for example, be used for the purpose of the present invention. Various nutrients which may be used are exemplified as follows. Thus, for example, glucose, starch, dextrin, mannose, fructose, sucrose, lactose, xylose, arabinose, mannitol, waste molasses and the like may be used as carbon sources alone or in combination, although it is possible to use, depending upon the assimilability of the strain used, various hydrocarbons, alcohols and organic acids. Ammonium chloride, ammonium sulfate, ammonium nitrate, sodium nitrate, urea, peptone, meat extract, yeast extract, dry yeast, corn steep liquor, soybean meal and casamino acid may for example be used as a nitrogen source, alone or in combination. If desired, various inorganic salts such as, for example, sodium chloride, potassium chloride, magnesium chloride, calcium carbonate, potassium mono- or di-hydrogen phosphate, ferrous sulfate, calcium chloride, manganese sulfate, zinc sulfate, copper sulfate and the like may be used alone or in combination. Moreover, for example, vitamin B, biotin and other trace compounds may conveniently be used to promote the growth of the microorganism and to enhance the production of the desired DC-45 substances of the present invention.

For the fermentation of the desired substances of the present invention, liquid culturing procedures, in particular submerged culturing with stirring are preferred. The fermentation is preferably effected at a temperature of from 25° to 40° C. (for example, 28° to 38° C.). The pH of the medium is preferably from 4 to 10 (for example 6 to 8) which may be adjusted by adding, for example, aqueous ammonia or ammonium carbonate solution to the medium. In general, the desired substances DC-45-$A_1$ and/or DC-45-$A_2$ may be produced and accumulated in the culture broth by effecting the liquid culturing for 1 to 7 days. When the amount of the desired substance(s) in the culture broth reaches its maximum, the fermentation is discontinued.

The culture broth is then filtered to separate the microbial cells from the filtrate. Any and all of the desired substances of the present invention may be isolated and purified by various methods conventionally used to separate and purify various metabolic products present in the culture broth of microorganisms. For example, after separation of the cells from the culture broth, the cellfree filtrate having a pH of 6.0 is passed through a column packed with a non-ionic resin (for example, Diaion HP-20, commercially available from Mitsubishi Kasei Kogyo K.K., Tokyo) to adsorb the active substances onto the resin, from which the active substances may be eluted by using, for example, methanol, acetone or ethyl acetate. The eluted fractions are concentrated to dryness. Celite powders are used to absorb the active substances, and the powders are chromatographed by using a column packed with silica gel which has been suspended in chloroform.

Chloroform and a mixture of chloroform/methanol (200:1 v/v) are successively passed through the column to remove impurities, and then the column is eluted by using a mixture of chloroform/methanol (150:1 v/v) to give the fractions containing DC-45-A. A mixture of chloroform/methanol (100:1 v/v) is then applied to the column to elute the fractions containing DC-45-A$_1$. The following elution using a solvent system of chloroform/methanol (70:1 v/v) gives the fractions containing DC-45-B$_1$. Finally, a mixture of chloroform/methanol (50:1 v/v) is used to elute the fractions containing a mixture of DC-45-A$_2$ and DC-45-B$_2$. The fractions containing DC-45-A$_1$ and DC-45-A$_2$ are respectively combined and concentrated to dryness.

The fraction containing DC-45-A$_1$ is chromatographed by using a column packed with silica gel which has been suspended in a mixture of cyclohexane/ethyl acetate (1:1 v/v). A mixture of cyclohexane/ethyl acetate (1:1 v/v) is passed through the column to remove impurities, and the column is eluted by using a mixture of cyclohexane/ethyl acetate (1:3 v/v) so that DC-45-A$_1$ is eluted in substantially pure form, concentrated and treated with n-hexane to obtain powders of DC-45-A$_1$.

The fraction containing DC-45-A$_2$ is chromatographed by using a column packed with silica gel which has been suspended in a mixture of chloroform/ethyl acetate (1:1 v/v). A mixture of ethyl acetate/chloroform (1:1 v/v) is passed through the column to remove impurities, and the column is eluted by using a mixture of ethyl acetate/chloroform (5:1 v/v) to elute DC-45-A$_2$ in substantially pure form which is concentrated and treated with n-hexane to yield powders of DC-45-A$_2$.

From the general formulae of DC-45-A, DC-45-A$_1$, DC-45-A$_2$, it will be appreciated that DC-45-A$_2$ may be used as starting material for the preparation of DC-45-A$_1$ and its derivatives. It is also possible to prepare DC-45-A$_1$ and DC-45-A$_2$ by acid hydrolysis of DC-45-A or DC-45-B$_2$.

Thus according to a further feature of the present invention there is provided a process for preparing the compound DC-45-A$_1$ which comprises subjecting a compound of the general formula (B):

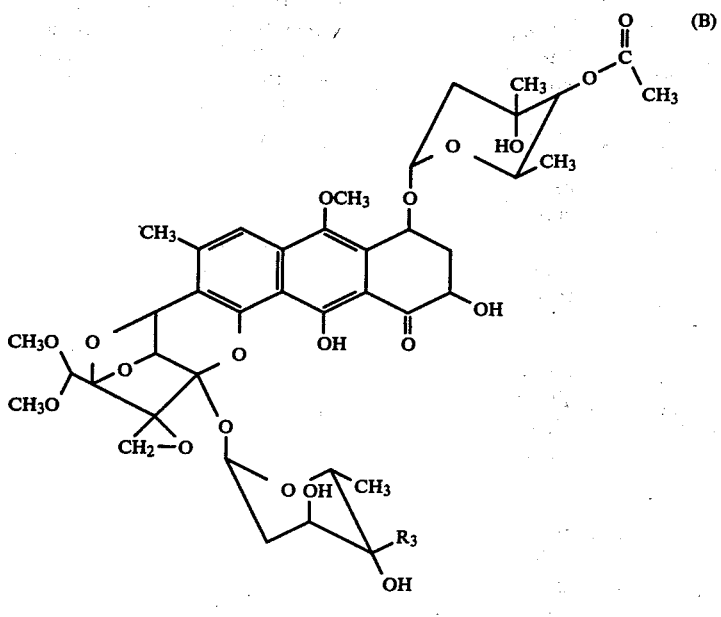

(wherein R$_3$ represents a group of the formula

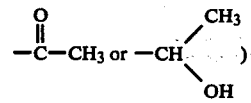

to acid hydrolysis and recovering DC-45-A$_1$ from the hydrolysis mixture.

According to a still further feature of the present invention there is provided a process for preparing the compound DC-45-A$_2$ which comprises subjecting the compound DC-45-A$_1$ or a compound of formula B as hereinbefore defined to acid hydrolysis and recovering the compound DC-45-A$_2$ from the hydrolysis mixture.

Acid hydrolysis may be effected in the following manner.

(A) Preparation of DC-45-A$_1$:

DC-45-A and/or DC-45-B$_2$ is subjected to acid hydrolysis using for example hydrochloric acid or sulfuric acid conveniently in the presence of an organic solvent such as, for example, methanol, acetone and the like. The product is then neutralized for example using lead carbonate. The resultant precipitate e.g. lead chloride or lead sulfate and for example the excess lead carbonate are removed from the reaction mixture by filtration. The filtrate may be chromatographed using a column packed with silica gel which has been suspended in chloroform. Chloroform and a mixture of chloroform/methanol (200:1 v/v) are successively passed through the column to remove impurities, and the column is eluted by using a mixture of chloroform/methanol (100:1 v/v) to obtain the fractions containing DC-45-A$_1$. The fractions are concentrated and chromatographed by using a column packed with silica gel which has been suspended in a mixture of cyclohexane/ethyl acetate (1:1 v/v). A mixture of cyclohexane/ethyl acetate (1:1 v/v) is used to elute the fraction containing DC-45-A$_1$ without impurities. The resultant fraction is concentrated to yield pure DC-45-A$_1$.

(B) Preparation of DC-45-A$_2$:

DC-45-A, DC-45-B$_2$ and/or DC-45-A$_1$ is subjected to acid hydrolysis using for example, hydrochloric acid or sulfuric acid, conveniently in the presence of an organic solvent such as, for example, methanol and acetone. In this case, it is preferred to effect the acid hydrolysis for a longer period of time and/or to use the acid at a higher concentration than in the case of the preparation of DC-45-A$_1$. The decomposed product is then neutralized for example by using lead carbonate. The resultant precipitate e.g. lead chloride or lead sulfate and for example the excess lead carbonate are removed from the reaction mixture by filtration. The filtrate is chromatographed by using a column packed with silica gel which has been suspended in a mixture of chloroform/ethyl acetate (1:1 v/v) to remove impurities, and the column is eluted by using a mixture of ethyl acetate/chloroform (5:1 v/v) to obtain the fractions containing DC-45-A$_2$ without impurities. The resultant fractions are combined and concentrated to dryness to yield DC-45-A$_2$ in pure form.

In both cases (A) and (B) the acid hydrolysis may be effected at a convenient temperature, for example, from ambient to the boiling point of the reaction mixture.

According to another feature of the present invention, there is provided a pharmaceutical composition for human or veterinary use, comprising as active ingredient a compound of formula I (e.g. DC-45-A$_1$ and/or DC-45-A$_2$) or a pharmacologically acceptable salt thereof in association with a pharmacologically acceptable carrier or excipient. The composition may be presented in a form suitable for oral, rectal or parenteral administration. Thus, for example, composition for oral administration may be solid or liquid and may be in the form of granules, tablets, coated tablets, capsules, syrups, emulsions, suspensions or drops, such compositions comprising carriers or excipients conventionally used in the pharmaceutical art. Thus, for example, suitable tabletting excipients include lactose, potato and soluble starches and magnesium stearate.

For parenteral administration, the carrier may be a sterile, parenterally acceptable liquid such as, for example, water, a physiological solution of sodium chloride, glucose solution, or a pharmaceutically acceptable oil such as, for example, arachis oil, contained in ampoules.

Compositions for rectal administration may take the forms of suppositories, the carriers comprising a suitable suppository base. Advantageously, the composition may be formulated as dosage units, each being adapted to supply a fixed dose of the active ingredient. Tablets, coated tablets, capsules, suppositories and ampoules are examples of suitable dosage unit forms.

The active ingredient may be a salt of DC-45-A$_1$ and/or DC-45-A$_2$, for example, with an alkali metal, alkaline earth metal, aluminium and the like such as sodium, potassium, calcium, magnesium, aluminium and the like, which may be prepared by using a hydroxide or alkoxide of an appropriate metal in conventional manner.

The present invention also provides DC-45-A$_1$ and/or DC-45-A$_2$ hereinbefore defined or a pharmacologically acceptable salt thereof for use as an antibiotic.

For use as antibiotic agents, it is preferred to administer DC-45-A$_1$ (for Example, at a dose of 0.001 to 0.05 mg/kg) and DC-45-A$_2$ (for example, at a dose of 0.02 to 1.0 mg/kg) once daily by intravenous injection, DC-45-A$_1$ and DC-45-A$_2$ being dissolved for example in a physiological solution of sodium chloride or a glucose solution conventionally used for the preparation of injecting agents. However, the dose may vary, depending upon various conditions such as, for example, the age and symptoms of the patient, and the times of the administration may also vary, depending for example, upon the amount of the compound to be administered and may be administered, for example, once within a week or once within a month.

If desired, it is also possible to administer DC-45-A$_1$ and DC-45-A$_2$ orally at the corresponding dose (for example, 3–10 times the dose of the oral administration).

The following non-limiting examples illustrate the present invention, in which the substances designated DC-45-A, DC-45-B$_1$, DC-45-B$_2$, DC-45-A$_1$ and DC-45-A$_2$ were respectively traced by their strong fluorescences.

EXAMPLE 1

*Streptomyces bottropensis* (formerly designated *Streptomyces ochraceus* DC-45) (FERM-P No. 5219; NRRL 12051) is used as the seed strain. The seed strain is inoculated into a seed medium [15 liter; containing KCl (4 g/l), MgSO$_4$.7H$_2$O (0.05 g/l), KH$_2$PO$_4$ (1.5 g/l), ammonium sulfate (5 g/l), sucrose (20 g/l), fructose (10 g/l), glucose (10 g/l), corn steep liquor (5 g/l) and CaCO$_3$ (20 g/l); pH 7.0 before sterilization, adjusted with NaOH] in a 30 liter jar fermenter. The fermentation is effected at 30° C. for 48 hours with stirring (220 r.p.m./min.) to obtain a seed culture which is transferred into a 300 liter jar fermenter containing a medium (150 liter) having the composition as hereinafter defined at a ratio of 5% (v/v).

Composition of the fermentation medium:

Glucose (30 g/l), soluble starch (10 g/l), Farmamedia (10 g/l; cotton seed meal, commercially available from Traders Oil Mill Co., U.S.A.), K$_2$HPO$_4$ (1 g/l), MgSO$_4$.7H$_2$O (1 g/l), NaCl (3 g/l), CuSO$_4$.5H$_2$O (70 mg/l), FeSO$_4$.7H$_2$O (10 mg/l), MnCl$_2$.4H$_2$O (8 mg/l), ZnSO$_4$.7H$_2$O (2 mg/l) and CoCl$_2$.6H$_2$O (0.006 mg/l); pH 7.0 before sterilization, adjusted with NaOH.

The pH of the medium is not controlled during the fermentation which is effected at 30° C. for 72 hours with shaking and aeration (180 r.p.m./150 liter/min.).

After completion of the fermentation, the microbial cells and precipitates are removed from the cultured broth by filtration, resulting in a filtrate (130 liter). The filtrate is passed through a column packed with 10 liters of a non-ionic porous resin (Diaion HP-10, commercially available from Mitsubishi Kasei Kogyo K.K., Tokyo) to adsorb the active substances onto the resin which is then washed with water (about 20 liter), followed by washing with 50% (v/v) methanol (about 20 liter) to remove impurities. After this elution is effected by using methanol. The methanol fractions, about 10 liter in total are collected, combined and concentrated to dryness in vacuo, and the dried material is dissolved in 0.1M phosphate buffer solution (pH 7.0). The solution is extracted three times with an equal amount of ethyl acetate. The ethyl acetate layers are combined and concentrated and the concentrate is adsorbed onto Celite to obtain a powder.

Separately, the microbial cells (wet weight about 2 kg) are suspended in acetone (about 50 liter) to extract the active substances. The extract is concentrated to dryness in vacuo and the dried material is dissolved in a 0.1M phosphate buffer solution (pH 7.0). The solution is extracted three times with ethyl acetate. The ethyl acetate layers are collected, combined and concentrated, and the concentrate is adsorbed onto Celite to obtain a powder.

These powders are combined and carefully put on a column packed with silica gel (Wako Gel, commercially available from Wako Junyaku K.K., Japan; 5 liter) which has been suspended in chloroform. Chloroform and a mixture of chloroform/methanol (200:1 v/v) are successively passed through the column to remove impurities, and then the column is eluted by using a solvent system of chloroform/methanol (150:1 v/v) to obtain the fractions containing DC-45-A. By subsequent elution by using a mixture of chloroform/methanol (100:1 v/v), the fractions containing DC-45-A$_1$ are obtained. After this, the fractions containing DC-45-B$_1$ are obtained by elution using a mixture of chloroform/methanol (70:1 v/v). At last, the fractions containing both DC-45-A$_2$ and DC-45-B$_2$ are obtained by elution using a mixture of chloroform/methanol (50:1 v/v).

The fractions containing DC-45-A$_1$ are collected, combined and concentrated to dryness in vacuo in the following manner. The combined fractions containing DC-45-A$_1$ are chromatographed by using a column packed with silica gel which has been suspended in a mixture of cyclohexane/ethyl acetate (1:1 v/v). A mixture of cyclohexane/ethyl acetate (1:1 v/v) is passed through the column to remove impurities, and the column is eluted by using a mixture of cyclohexane/ethyl acetate (1:3 v/v) to obtain the fractions containing DC-45-A$_1$ which are collected, combined and concentrated to dryness. n-Hexane is added to the dried material to yield a powder of DC-45-A$_1$ (15 mg).

The fractions containing DC-45-A$_2$ and DC-45-B$_2$ are collected, combined and concentrated to dryness. The dried material is chromatographed by using a column packed with silica gel which has been suspended in a mixture of chloroform/ethyl acetate (1:1 v/v) in the following manner. A similar mixture of chloroform/ethyl acetate is passed through the column to remove impurities, and the column is eluted by using a mixture of ethyl acetate/chloroform (5:1 v/v) to obtain the fractions containing DC-45-A$_2$ which are collected, combined and concentrated to dryness. The dried material is treated with n-hexane to yield a powder of DC-45-A$_2$.

EXAMPLE 2

DC-45-A (500 mg) is dissolved in a 0.1% hydrochloric acid/methanol solution (10 ml) and the solution is allowed to stand at room temperature for 4 hours. Then, lead carbonate (100 mg) is added to the reaction mixture for neutralization. The solution is filtered, and the filtrate is concentrated to dryness and chromatographed by using a column packed with silica gel which has been suspended in chloroform. Chloroform and a mixture of chloroform/methanol (200:1 v/v) are successively passed through the column to remove impurities, and a solvent system of chloroform/methanol (120:1 v/v) is used for elution of the fractions containing DC-45-A$_1$.

The fractions are collected, combined and concentrated. The concentrate is chromatographed by using a column packed with silica gel which has been suspended in a mixture of cyclohexane/ethyl acetate (1:1 v/v). A mixture of cyclohexane/ethyl acetate (1:1 v/v) is passed through the column to remove impurities, and the column is eluted by using a solvent system of cyclohexane/ethyl acetate (1:3 v/v) to obtain the fractions containing DC-45-A$_1$ which are collected, combined and concentrated to dryness. The dried material is treated with n-hexane to yield a powder of DC-45-A$_1$.

EXAMPLE 3

DC-45-A (500 mg) is dissolved in a 0.1% hydrochloric acid/methanol solution (10 ml) and allowed to stand at room temperature for 8 hours. Then, lead carbonate is added to the reaction mixture for neutralization. The mixture is filtered to remove the resultant lead chloride and the excess lead carbonate, and the filtrate is concentrated to dryness. The concentrate is chromatographed by using a column packed with silica gel which has been suspended in chloroform. Chloroform and a mixture of chloroform/methanol (120:1 v/v) are successively passed through the column to remove impurities. Then a solvent system of chloroform/methanol (60:1 v/v) is used to elute the fractions containing DC-45-A$_2$ which are collected, combined and concentrated to dryness. The dried material is chromatographed by using a column packed with silica gel which has been suspended in a mixture of chloroform/ethyl acetate (1:1 v/v). The mixture of chloroform/ethyl acetate (1:1 v/v) is passed through the column to remove impurities, and the column is eluted by using a solvent system of chloroform/ethyl acetate (1:5 v/v) to obtain the fractions containing DC-45-A$_2$ which are collected, combined and concentrated to dryness, followed by treating with n-hexane to yield a yellow powder of DC-45-A$_2$ (120 mg).

EXAMPLE 4

DC-45-A$_1$ (200 mg) obtained by the method of Example 3 is dissolved in a 0.1% hydrochloric acid/methanol solution (5 ml) and allowed to stand at room temperature for 4 hours. Lead carbonate (50 mg) is added to the reaction mixture for neutralization. The mixture is then filtered to remove the resultant lead chloride and the excess of lead carbonate added. The filtrate is concentrated to dryness and treated in a similar manner to that described in Example 4 to yield DC-45-A$_2$ (95 mg).

EXAMPLE 5

Preparation of parenteral injection:

DC-45-A$_2$ (2.0 g) is dissolved in distilled water (1000 ml) and made aseptic by using a Millipore filter (pore size 0.22μ; commercially available from Millipore Corpn., U.S.A.). The aseptic filtrate thus obtained is divided into fractions (each 5 ml), each of which is put into a brown vial so that each vial contained 10 mg of DC-45-A$_2$. The vials are left to stand at an atmospheric temperature of −50° C. for 24 hours to freeze the contents and are then subjected to primary drying at an atmospheric temperature of −10° C. for 24 hours under a pressure of 0.1 mmHg. After confirmation of the temperature of the contents being the same as the atmospheric temperature, the second drying is effected at an atmospheric temperature of 40° C. for 4 hours under a pressure of 0.1 mmHg to remove moisture content. After this, the vials are sealed using rubber stoppers. In use, a sterilized physiological solution of sodium chloride (each 5 ml) is added to each vial with stirring so that the ingredient dissolved to obtain an injection solution.

We claim:

1. A compound of formula I:

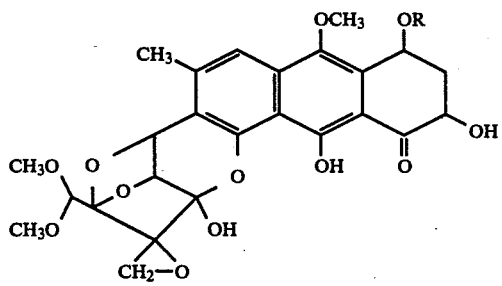

wherein R represents the group:

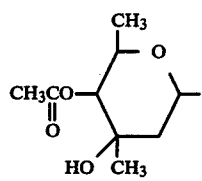

or a hydrogen atom and the salts thereof chosen from the group consisting of sodium, potassium, calcium, magnesium and aluminium salts.

2. A compound as claimed in claim 1 represented by the formula:

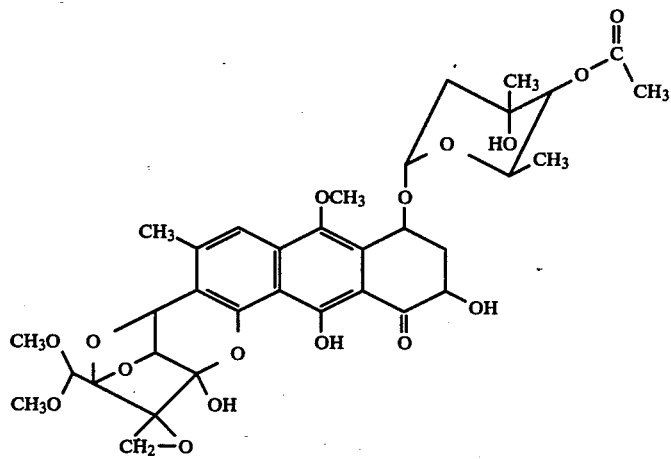

or a salt thereof chosen from the group consisting of sodium, potassium, calcium, magnesium and aluminium salts.

3. A compound as claimed in claim 1 represented by the formula:

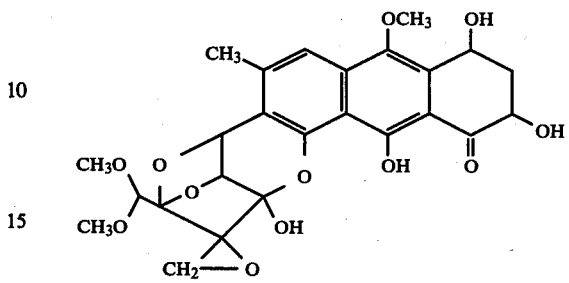

or a salt thereof chosen from the group consisting of sodium, potassium, calcium, magnesium and aluminium salts.

4. A pharmaceutical composition comprising an antibacterial effective amount of a compound of claim 1 in combination with a pharmaceutically acceptable carrier or excipient.

5. A process for inhibiting bacterial growth in a patient or animal in need thereof comprising administering to said patient or animal an antibacterial effective amount of the composition of claim 4.

* * * * *